June 5, 1973 W. H. JESSEL. JR., ET AL Plant Pat. 3,353
CHRYSANTHEMUM PLANT
Filed Aug. 31, 1971
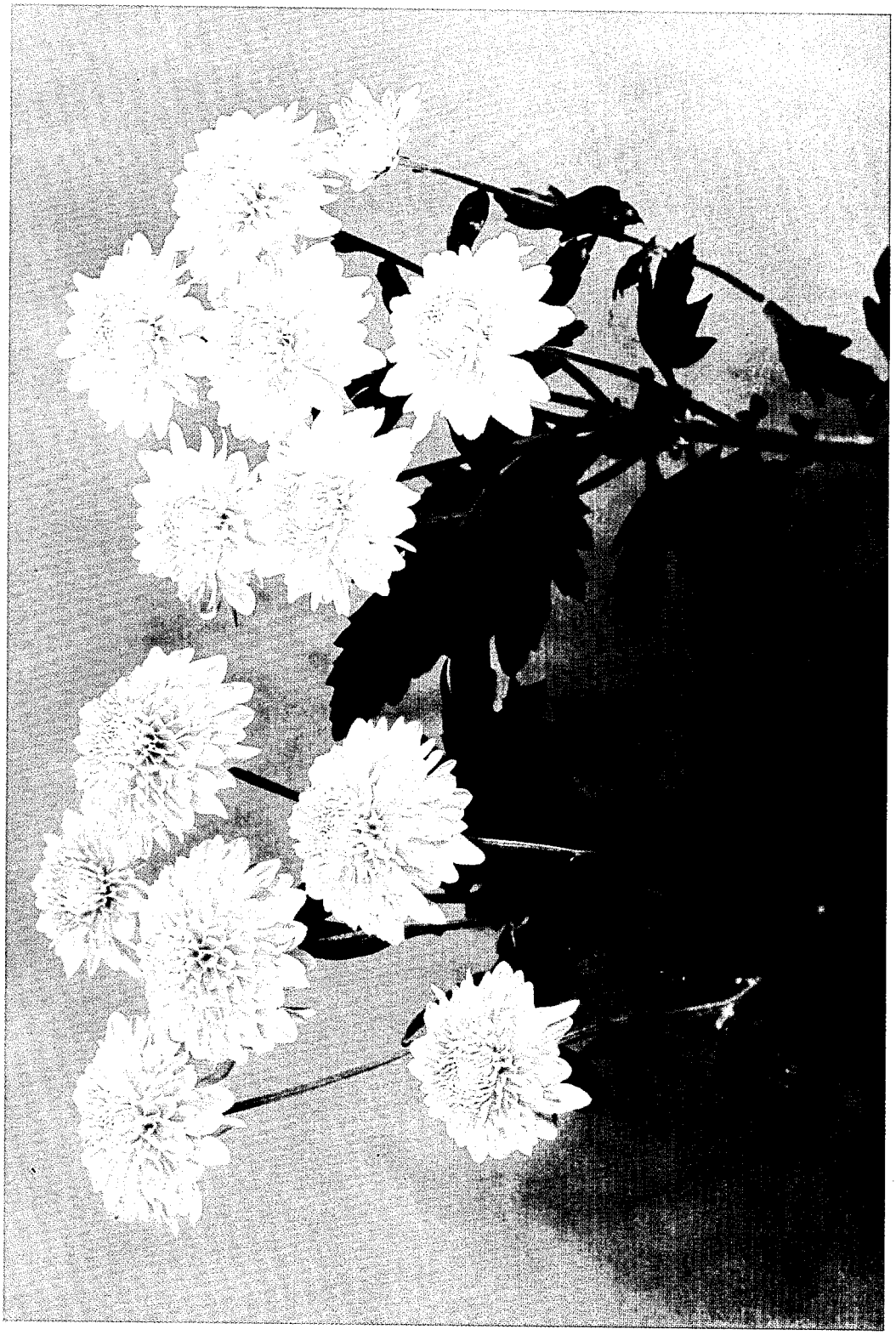

United States Patent Office

Plant Pat. 3,353

Patented June 5, 1973

3,353
CHRYSANTHEMUM PLANT

Walter H. Jessel, Jr., Doylestown, and William E. Duffett, Akron, Ohio, assignors to Yoder Brothers, Inc., Barberton, Ohio

Filed Aug. 31, 1971, Ser. No. 176,756

Int. Cl. A01h *5/00*

U.S. Cl. Plt.—79 1 Claim

The present invention comprises a new and distinct cultivar of chrysanthemum plant which is a sport of the cultivar known in the United States as Belair, which forms the subject matter of pending U.S. plant patent application Ser. No. 58,750, filed July 27, 1970, and now P.P. 3,184.

The new cultivar is similar in many respects to Golden Belair, which is disclosed and illustrated in pending U.S. application Ser. No. 58,751, filed July 27, 1970, and now P.P. 3,185, having the same characteristics as Golden Belair of:

(1) Flower size.
(2) Same recommended period of flowering.
(3) Foliage size and color.

The new cultivar is distinguished from Golden Belair by the following characteristics, when grown under comparable conditions:

(1) A more intense flower color.
(2) The flower color under high light and temperature conditions is a truer bronze rather than a golden bronze or yellow.
(3) A higher flower crown and more formal flower form.
(4) Three to four days earlier response.
(5) A more uniform response within a flowering plot.
(6) 2" shorter habit.

The new cultivaor is also similar in many respects to Bronze Belair, which is illustrated and described in pending U.S. application Ser. No. 58,749, filed July 27, 1970, and now P.P. 3,183, having the same characteristics as Bronze Belair of:

(1) Equal vigor.
(2) Same recommended period of flowering.
(3) Foliage size and color.
(4) Flowering response.

The new cultivar is distinguished from Bronze Belair by the following characteristics:

(1) More intense bronze flower color.
(2) Better color retention under high light, high temperature conditions and also as the flower matures.
(3) Flowers approximately one half inch larger in diameter.
(4) A higher flower crown and more formal flower form.

The new cultivar was selected from a flowering block of the parent cultivar at Barberton, Ohio, and when asexually reproduced by cuttings at Barberton, Ohio, has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from April through November; coastal California, January through December; and Florida, December through April.

The accompanying photographic drawing shows the unique characteristics of the new cultivar, the color being as nearly true as possible with color illustrations of this type. In the drawing, the new cultivar appears on the left and the cultivar Golden Belair on the right.

In the description which follows, color references are made to the Munsell Color Book, 1963 edition, and comparisons are made with the cultivars Golden Belair and Bronze Belair. Where only a single value or description appears for the new cultivar, such value or description applies to the comparison cultivar as well.

Botanical classification: *Chrysanthemum morifolium*

| | Flame Belair | Golden Belair | Bronze Belair |
|---|---|---|---|
| Bloom: | | | |
| Size | 3" | 3" | 2½". |
| Fully expanded | 3½" | 3½" | 3". |
| Borne | Terminal cluster of 8–12 on elongated pedicels according to culture. | | |
| Stems | Elongated pedicels | | |
| Form | Decorative | | |
| permanence | 7–10 days | | |
| Color: | | | |
| Center of flower | Orange bronze, 5YR6/12 | Orange yellow, 8.75YR6/12 to 7.5YR7/12. | Orange bronze, 2.5YR5/10 to light bronze, 10YR8/10. |
| Base of petals | Yellow 5Y8.5/12 | Yellow 3.75Y8/12 | Bronze, 2.5YR5/10. |
| Inside of petals | Orange to bronze, 1.25YR5/12 to 8.75YR6/12 | Yellow, 2.5Y8/10 to yellow, 1.25YR8/14. | Bronze, 2.5YR5/10 to light bronze, 10YR8/10. |
| Reverse of petals | Gold to yellow, 1.25Y7/12 to 5Y8/10 | Yellow, 2.5Y8.5/10 | Light yellow, 2.5Y8.5/6. |
| Tonality from a distance | Orange bronze | Golden bronze | Orange bronze to light bronze. |
| Discoloration | Orange bronze, 1.25YR5/12 | Yellow, 1.25YR8/14 | Light bronze, 10YR8/10. |
| Petals: | | | |
| Texture | Smooth | Smooth | Smooth. |
| Appearance and form | Slightly open at base, broadens quickly to flat keel, tapering to a blunt point with recurved edges. | Slightly open at base, keeled at mid point, tapering to a blunt point. | Slightly open at base, keeled at mid point, tapering to a blunt point. |
| Arrangement | Composite, whorled on a single receptacle | | |
| Persistence | Resist shatter | | |
| Fragrance | Typical chrysanthemum | | |
| Reproductive organs: | | | |
| Stamen, anthers | None to 20, more or less depending on culture | | |
| Pollen | None to scant | | |
| Arrangement | Clustered in center of flower, if present | | |
| Styles | Present in both ray and disc florets | | |
| Length | Short | | |
| Ovaries | At the base of petal attached to receptacle | | |
| Plant: | | | |
| Form | Herbaceous | | |
| Growth | Upright | | |
| Height | Approximately 36"–42" when given 1 to 3 long day weeks and a total crop time of 10 to 12 weeks for the various recommended seasons of the year as defined in the timetables of Yoder Bros., Inc., Barberton, Ohio. | Approximately 38"–44" when given 1 to 3 long day weeks and a total crop time of 10 to 12 weeks for the various recommended seasons of the year as defined in the timetables of Yoder Bros., Inc., Barberton, Ohio. | Approximately 38"–42" when given 1 to 3 long day weeks and a total crop time of 10 to 12 weeks for the various recommended seasons of the year as defined in the timetables of Yoder Bros., Inc., Barberton, Ohio. |

TABLE—Continued

| | Flame Belair | Golden Belair | Bronze Belair |
|---|---|---|---|
| Spread | None when grown single stem to little when pinched. | | |
| Foliage: | | | |
| Top side | Dark green, 7.5GY3/4 | | |
| Size | 7"–9" long, 4"–5" wide | | |
| Quantity | Numerous | | |
| Shape | Spatulate lobed | | |
| Texture | Coarse | | |
| Ribs and veins | Prominent | | |
| Edge | Deeply indented | | |
| Serration | Slight | | |
| Under side | Light green, 7.5GY4/4 | | |
| Stipules | Prominent at base of petiole | | |

We claim:

1. A new and distinct cultivar of crysanthemum characterized particularly as to its uniqueness when compared to the cultivar Golden Belair by its more intense bronze flower color, particularly under high light and temperature conditions, higher flower crown and more formal flower form, three to four days earlier and more uniform response, and its 2 inch shorter habit; and characterized as to uniqueness when compared to the cultivar Bronze Belair by its more intense bronze color and better color retention under high light and high temperature conditions and during maturity of flower.

No references cited.

ROBERT E. BAGWELL, Assistant Examiner